US012703630B2

(12) United States Patent
Alderson

(10) Patent No.: US 12,703,630 B2
(45) Date of Patent: Aug. 11, 2026

(54) PEROXIDE STABILIZERS

(71) Applicant: DIVERSEY, INC., Fort Mill, SC (US)

(72) Inventor: Faraz Alderson, Mississauga (CA)

(73) Assignee: Diversey, Inc., Fort Mill, SC (US)

(*) Notice: Subject to any disclaimer, the term of this patent is extended or adjusted under 35 U.S.C. 154(b) by 1213 days.

(21) Appl. No.: 17/088,818

(22) Filed: Nov. 4, 2020

(65) Prior Publication Data

US 2021/0061659 A1 Mar. 4, 2021

Related U.S. Application Data

(62) Division of application No. 15/815,977, filed on Nov. 17, 2017, now Pat. No. 10,858,249.

(Continued)

(51) Int. Cl.

*C01B 15/037* (2006.01)
*C01B 15/12* (2006.01)

(Continued)

(52) U.S. Cl.

CPC .......... *C01B 15/037* (2013.01); *C01B 15/123* (2013.01); *C01D 1/04* (2013.01);

(Continued)

(58) Field of Classification Search

CPC ....... C01B 15/037; C01B 15/123; C01D 1/04; C07D 317/38; C07D 319/06; C07F 9/3808; C07F 9/3839; C07F 9/386

(Continued)

(56) References Cited

U.S. PATENT DOCUMENTS 3,387,939 A * 6/1968 Reilly .................. C01B 15/037 252/186.28
3,860,391 A * 1/1975 Kling ........................ D06L 4/12 252/186.25

(Continued)

FOREIGN PATENT DOCUMENTS

CA 2130178 9/1993
CN 102712473 A * 10/2012 ............... D06L 4/12

(Continued)

OTHER PUBLICATIONS

Machine Translation of CN 102712473 A. (Year: 2012).*

(Continued)

*Primary Examiner* — Coris Fung
*Assistant Examiner* — Catriona M Corallo
(74) *Attorney, Agent, or Firm* — Ingrassia Fisher & Lorenz LLP

(57) ABSTRACT

Methods for stabilizing one or more peroxide compounds in solution comprising adding to the solution an effective amount of at least one compound selected from the group comprising (i) cyclic carbonates; (ii) poly-phosphonic acid chelating agents and salts thereof, and alkaline pH adjusting agents with a pKb value of up to 3.0, wherein the w/w ratio of the poly-phosphonic acid chelating agent or salt thereof to alkali or alkaline earth metal hydroxide is from about 1:1 to about 50:1; and (iii) mixtures thereof. Also disclosed are solutions comprising the above compounds, uses of the above compounds to stabilize peroxide compounds in solutions, and compounds recited above for use as novel stabilizers.

16 Claims, 2 Drawing Sheets

Related U.S. Application Data

(60) Provisional application No. 62/424,608, filed on Nov. 21, 2016.

(51) Int. Cl.
*C01D 1/04* (2006.01)
*C07D 317/38* (2006.01)
*C07D 319/06* (2006.01)
*C07F 9/38* (2006.01)

(52) U.S. Cl.
CPC ......... *C07D 317/38* (2013.01); *C07D 319/06* (2013.01); *C07F 9/3808* (2013.01); *C07F 9/3839* (2013.01); *C07F 9/386* (2013.01)

(58) Field of Classification Search
USPC .......................................................... 423/272
See application file for complete search history.

(56) References Cited

U.S. PATENT DOCUMENTS

| | | | | |
|---|---|---|---|---|
| 3,903,244 | A * | 9/1975 | Winkley | C01B 15/037 423/272 |
| 4,061,721 | A * | 12/1977 | Strong | C01B 15/037 423/272 |
| 4,070,442 | A * | 1/1978 | Watts | C01B 15/037 423/272 |
| 4,812,173 | A | 3/1989 | Tsao et al. | |
| 6,040,284 | A | 3/2000 | Marquis et al. | |
| 6,479,445 | B1 | 11/2002 | Machac, Jr. | |
| 6,927,237 | B2 | 8/2005 | Hei et al. | |
| 7,887,641 | B2 | 2/2011 | Man et al. | |
| 8,246,758 | B2 | 8/2012 | Man et al. | |
| 8,999,357 | B2 | 4/2015 | Elfersy et al. | |
| 8,999,363 | B2 | 4/2015 | Elfersey | |
| 9,133,417 | B2 | 9/2015 | Tajmamet et al. | |
| 9,233,180 | B2 | 1/2016 | Omidbakhsh et al. | |
| 2004/0259745 | A1 | 12/2004 | Asher et al. | |
| 2007/0049510 | A1 | 3/2007 | Fujii et al. | |
| 2007/0065475 | A1 | 3/2007 | Elfersy | |
| 2007/0087954 | A1* | 4/2007 | Wang | C11D 3/046 510/375 |
| 2012/0288570 | A1* | 11/2012 | Zhu | D06L 4/12 252/186.28 |
| 2013/0203849 | A1 | 8/2013 | Yehuda | |
| 2013/0272984 | A1 | 10/2013 | Klug | |
| 2014/0097144 | A1 | 4/2014 | Li et al. | |
| 2014/0147402 | A1 | 5/2014 | Klug | |

FOREIGN PATENT DOCUMENTS

| | | | |
|---|---|---|---|
| JP | 54137445 | | 10/1979 |
| JP | 2002502450 | A | 1/2002 |
| JP | 2016008174 | A | 1/2016 |
| WO | 1997-029158 | | 8/1997 |
| WO | 9932216 | A1 | 7/1999 |
| WO | 2016-027735 | | 2/2016 |
| WO | 2016-082897 | | 6/2016 |
| WO | 2017004529 | A1 | 1/2017 |

OTHER PUBLICATIONS

Office Action of counterpart EP Application No. 17872861.4 dated Apr. 23, 2021; 3 pages.
Office Action of counterpart AU Application No. 2017362143 dated Jun. 29, 2021; 3 pages.
Extended European Search Report of counterpart EP Application No. 17872861.4 dated Jun. 8, 2020; 6 pages.
Majekodunmi, et al., "Stability of Benzoyl Peroxide in Aromatic Ester-Containing Topical Formulations," Pharmaceutical Development and Technology, vol. 12, No. 6, Jan. 7, 2007; 12 pages.

* cited by examiner

PEROXIDE STABILIZERS

CROSS-REFERENCE TO RELATED APPLICATIONS

This application is a divisional of U.S. patent application Ser. No. 15/815,977, filed Nov. 17, 2017, which claims the benefit under 35 U.S.C. 119(e) of U.S. provisional patent application 62/424,608 filed Nov. 21, 2016; the content of both patent applications are incorporated by reference herein.

FIELD OF THE INVENTION

The present invention relates to stabilizers for peroxide compounds.

BACKGROUND OF THE INVENTION

It is known that peroxide compositions or solutions, such as compositions or solutions containing hydrogen peroxide, are susceptible to peroxide loss over time. To reduce the rate of peroxide loss, stabilizing agents such as chelating agents, acidifiers, and buffering agents have been used. Many conventional stabilizing agents are only effective in narrow pH ranges, usually within acidic ranges.

Poly-phosphonic acid chelating agents, such as 1-hydroxyethane-1,1-diphosphonic acid (HEDP, also referred to herein as etidronic acid and by the trade name DEQUEST 2010), aminotrimethylene phosphonic acid, di-ethylene triamine penta(methylene phosphonic acid), ethylene di-amine tetra(methylene phosphonic acid), hexamethylenediamine-tetra(methylene phosphonic) acid, salts thereof, are known to prevent catalytic degradation of peroxide compounds by free transition metal ions in solutions. A drawback of such poly-phosphonic acid chelating agents and salts thereof is their unfavorable environmental profile—the phosphorus can be released into the environment and contribute to the eutrophication of lakes and other bodies of water. HEDP can also cause surface corrosion when used in high concentrations.

Potassium hydroxide (KOH) is a base with many niche applications. It is used in solutions for cleaning (e.g. grease- and debris-removing) and to adjust the pH. While it is known to have microbicidal properties, its activity is low. The activity of KOH can be increased by raising the temperature and/or using higher concentrations. KOH is very corrosive and must be handled with care. It is used extensively in 'cleaning-in-place' systems, usually followed by an acid rinse to neutralize the KOH.

The present invention is intended to provide new peroxide stabilizing compounds, including compounds that are effective in both acidic and alkaline pH ranges.

SUMMARY OF THE INVENTION

The inventor has found, surprisingly, that cyclic carbonates, such as propylene carbonate and its analogs (e.g. ethylene carbonate, butylene carbonate and glycerol carbonate) can be used to stabilize peroxide compounds in solution. The benefits of using these cyclic carbonates as peroxide stabilizing agents are their relative low cost, high availability, and friendliness to the environment—e.g. they are readily biodegradable, have low volatility, are approved as safe food additives, and have low to no toxicity to living organisms. Other benefits include their ability to act as solvents to aid in solubilization of ingredients and cleaning soils, as well as effectiveness at a wide range of pH, e.g. from 0.1-14. This is unexpected since known peroxide stabilizers typically become less effective as the solution pH is increased. For example, conventional stabilizers such as EDTA, dipicolinic acid and acetanilide show minimal effectiveness in alkaline ranges. Yet another benefit is that cyclic carbonates have low freezing points (e.g. −49.degree. C. for propylene carbonate) and can therefore be useful in preventing solutions from freezing.

Also surprisingly, the inventor has found that the stabilizing effect of poly-phosphonic acid chelating agents and their salts can be achieved at much lower concentrations when an alkaline pH adjusting agent with a pKb value of up to 3.0 is added. This can lead to an improved environmental profile and cost reductions.

Accordingly, the present invention provides a stabilized peroxide solution containing a peroxide compound, and an effective amount of at least one compound selected from the group comprising (i) cyclic carbonates; (ii) a combination of (a) poly-phosphonic acid chelating agents and salts thereof, and (b) alkaline pH adjusting agents with a pKb value of up to 3.0, wherein the w/w ratio of the poly-phosphonic acid chelating agent or salt thereof to alkali or alkaline earth metal hydroxide is from about 1:1 to about 50:1; and (iii) mixtures thereof.

In accordance with another aspect, the invention provides the use of at least one compound selected from the group comprising, consisting essentially of, or consisting of (i) cyclic carbonates; (ii) a combination of (a) poly-phosphonic acid chelating agents and salts thereof, and (b) alkaline pH adjusting agents with a pKb value of up to 3.0, wherein the w/w ratio of the poly-phosphonic acid chelating agent or salt thereof to alkali or alkaline earth metal hydroxide is from about 1:1 to about 50:1; and (iii) mixtures thereof, in stabilizing a peroxide compound in solution.

In accordance with yet another aspect, the invention provides a method of stabilizing a peroxide compound in solution, the method comprising the step of adding at least one compound selected from the group comprising, consisting essentially of, or consisting of an effective amount of at least one compound selected from the group comprising (i) cyclic carbonates; (ii) a combination of (a) poly-phosphonic acid chelating agents and salts thereof, and (b) alkaline pH adjusting agents with a pKb value of up to 3.0, wherein the w/w ratio of the poly-phosphonic acid chelating agent or salt thereof to alkali or alkaline earth metal hydroxide is from about 1:1 to about 50:1; and (iii) mixtures thereof, to the peroxide compound in solution.

Still another aspect of the invention provides at least one peroxide stabilizer chosen from the group comprising, consisting essentially of, or consisting of (i) cyclic carbonates; (ii) a combination of (a) poly-phosphonic acid chelating agents and salts thereof, and (b) alkaline pH adjusting agents with a pKb value of up to 3.0; and (iii) mixtures thereof; for use in stabilizing a peroxide compound in solution.

The peroxide compound is selected from the group comprising, consisting essentially of, or consisting of hydrogen peroxide, hydrogen peroxide adduct, group IIIA oxidizing agent, or hydrogen peroxide donors of group VIA oxidizing agent, group VA oxidizing agent, group VIIA oxidizing agent, sodium peroxide, ureal peroxide, perboric acid, sodium/potassium perborate, sodium persulfate, perphosphate, calcium peroxide, lithium peroxide, sodium peroxide, dibenzoyl peroxide, diacetyl peroxide, di(n-propyl) peroxydicarbonate, butyl peroxybenzoate, butyl hydroperoxide, ethylidene peroxide, ethyl hydroperoxide, peroximonosulfuric acid, peroxycarboxylic acids (peracetic acid, peroctanoic acid, performic acid, peroxiphthalates, etc.), percarbonates (e.g. sodium percarbonates, potassium percarbonates), perbenzoic acid, cumene peroxide, or mixtures thereof.

In some embodiments, the cyclic carbonate is selected from the group comprising, consisting essentially of, or consisting of propylene carbonate, ethylene carbonate, butylene carbonate, and glycerol carbonate.

The solution can have a poly-phosphonic acid chelating agent or salt thereof selected from the group comprising, consisting essentially of, or consisting of 1-hydroxyethane 1,1-diphosphonic acid (HEDP), aminotrimethylene phosphonic acid, di-ethylene tri-amine penta(methylene phosphonic acid), ethylene di-amine tetra(methylene phosphonic acid), hexamethylenediamine-tetra(methylene phosphonic) acid, salts thereof, and mixtures thereof.

The alkaline pH adjusting agent with a pKb value of up to 3.0 can be selected from the group comprising, consisting essentially of, or consisting of potassium hydroxide (KOH), sodium hydroxide (NaOH), lithium hydroxide, magnesium hydroxide, calcium hydroxide, rubidium hydroxide, cesium hydroxide, strontium hydroxide, barium hydroxide, and mixtures thereof.

The solution can further comprise a solvent selected from the group comprising, consisting essentially of, or consisting of water, propylene glycol derivatives with ethoxylation and/or propoxylation, alkoxytriglycols and other glycols such as methoxytriglycol, ethoxytriglycol, butoxytriglycol, hexyltriglycol, propylene glycol methyl ether acetate, dipropylene glycol methyl ether acetate, dipropylene glycol n-butyl ether, propylene glycol n-butyl ether, dipropylene glycol n-propyl ether, propylene glycol n-propyl ether, dipropylene glycol methyl ether, tripropylene glycol methyl ether, benzyl alcohol, phenoxyethanol, phenethyl alcohol, methanol, ethanol, butyl 3-hydroxybutyrate, isopropyl alcohol, ethylhexylglycerol, branched or unbranched diols, charged or uncharged non-surfactant emulsifying agents, dibasic esters, polar protic solvents, polar aprotic solvents, and mixtures thereof.

Solutions according to the invention can be free of peroxide stabilizing agents, other than the compounds recited herein.

The cyclic carbonate can be present in a concentration from about 0.05, 1, 5, 10, or 15 wt. % or up to about 2.5, 7.5, 12.5, 17.5, 20, 30, 40 or 49 wt. %.

The weight ratio of the poly-phosphonic acid chelating agent or salt thereof to alkali or alkaline earth metal hydroxide can be from about 1:5 to about 100:1, or up to about 50:1, about 40:1, about 30:1, about 20:1, 10:1, about 5:1, or about 1:1.

The peroxide compound can be present in a concentration of from about 0.05, 0.5, 1, 2, 4, 7, 14, 16, 25, 35, or 45 wt. %, or up to about 50, 30, 20, 10, 8, 5, 3, 1.5, 0.1, or 0.01 wt. %.

The pH of the solution can be up to about 14, 12, 10, 8, 7, 6, 5, 4, 3, 2, or 1 and/or from about 0.1, 1.8, 2.5, 3.2, 3.8, 4.2 or 5.5.

BRIEF DESCRIPTION OF THE DRAWINGS

The invention may be better understood with references to the drawings, in which.

DETAILED DESCRIPTION OF THE EMBODIMENTS

Figure 1:
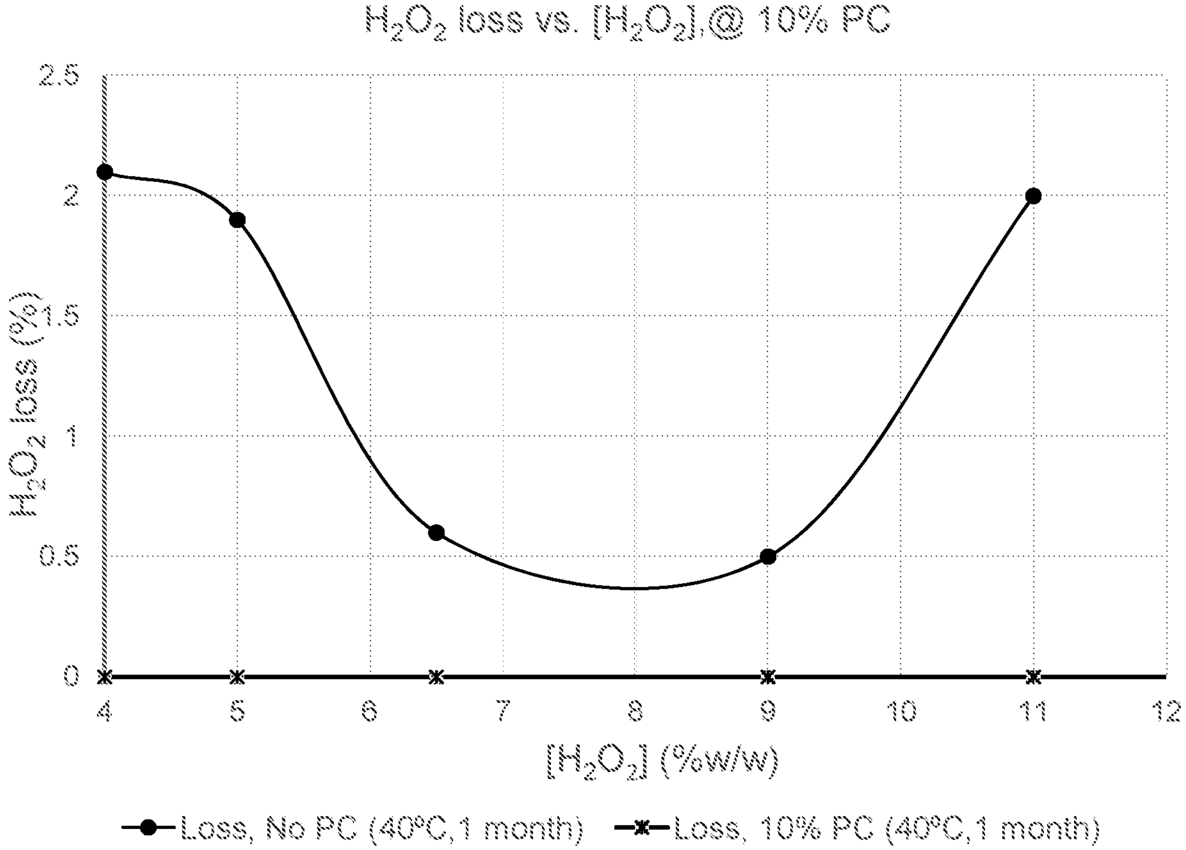
FIG. 1 is a graph showing the effect of hydrogen peroxide concentration on peroxide loss when propylene carbonate is present in the solution at a fixed concentration of 10 wt. %.

For the sake of clarity and to avoid ambiguity, certain terms are defined herein as follows.

The term "comprising" means "including without limitation." Thus, a composition comprising a list of ingredients may include additional ingredients not expressly recited. The term "consisting of" means "including the listed ingredients and such additional ingredients as may be present as natural or commercial impurities or additives." Natural and commercial impurities will be apparent to the person of ordinary skill in the art. An example of a commercial additive are minute quantities of stabilizers in hydrogen peroxide commercial solutions, for example. The term "consisting essentially of" means "consisting of" the listed ingredients (as defined herein) plus such additional ingredients as would not materially affect (positively or negatively) the basic and novel properties of the solution." By "basic and novel properties" is meant the stability of the solution as provided by the stabilizers according to the invention.

The present invention employs an "effective amount of at least one stabilizer". This is defined herein to be an amount that leads to an improvement in hydrogen peroxide stability by at least 10%, 15%, 20%, 30%, 40%, 50%, 60%, 70%, 80%, 90% or 100% when the effective amount of the stabilizing agents is present as compared to when it is not present, as measured using the accelerated aging test disclosed herein. The stabilizers of the invention are not used to enhance the antimicrobial efficacy of the base solution but merely to stabilize peroxide compounds in the solution.

The term "weight percent," "wt. %," "percent by weight," "% by weight," % w/w, and variations thereof refer to the concentration of a substance as the weight of that substance divided by the total weight of the composition and multiplied by 100.

The term "about" refers to a variation in the numerical quantity that can occur, for example, through typical measuring and liquid handling procedures used for making concentrates or ready-to-use (RTU) solutions in the real world, through differences in the manufacture, source, or purity of the ingredients used to make the compositions or carry out the methods, and the like. The term "about" also encompasses amounts that differ due to different equilibrium conditions or different reaction levels for a composition resulting from a particular initial mixture. Whether or not modified by the term "about," the claims include equivalents to the quantities.

In the description and claims, the singular forms "a," "an," and "the" include plural referents unless the content clearly dictates otherwise. Thus, for example, reference to a composition containing "a compound" includes a composition having two or more compounds. It should also be noted that the term "or" is generally employed in the sense of "and/or" unless the content clearly dictates otherwise.

Unless otherwise specified, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." The term "substituted alkyls" refers to alkyl groups having substituents replacing one or more hydrogens on one or more carbons of the hydrocarbon backbone. Such substituents may include, for example, alkenyl, alkynyl, halogena, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, am inocarbonyl, alkylaminocarbonyl, dialkylaminocarbonyl, alkylthiocarbonyl, alkoxyl, phosphate, phosphonate, phosphine, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including hetero aromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The present invention contemplates the possibility of omitting any components listed herein. The present invention further contemplates the omission of any components even though they are not expressly named as included or excluded from the invention.

The chemical structures herein are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

Peroxide Compounds

The novel peroxide stabilizers according to the present invention are useful in stabilizing peroxide compounds in solutions or compositions. When used herein, a "peroxide compound" is a compound containing an oxygen-oxygen single bond or the peroxide anion:

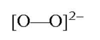

Examples include alkali metal peroxides (e.g. sodium peroxide). Also included are compounds that generate and release hydrogen peroxide when dissolved in aqueous solution (e.g. urea peroxide, perboric acid, sodium/potassium perborate, sodium persulfate, calcium peroxide, lithium peroxide, sodium peroxide, or other peroxides of alkali, alkaline earth, or transition group metals or salts thereof).

Still other examples are compounds according to the following formulas:

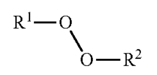

(I)

wherein R1 and R2 are independently a substituted or unsubstituted, branched or unbranched, cyclic or linear alkyl group. R1 and R2 may be connected to form a cyclic structure. Examples include dialkyl peroxides such as dibenzoyl peroxide, diacetyl peroxide, di(n-propyl) peroxydicarbonate, butyl peroxybenzoate, and many others commercially available under the brand name Luperox™. In certain cases, the R1 and R2 could be sulfurous or phosphorus atoms (e.g. peroxidisulfuric acid).

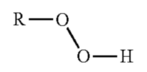

(II)

wherein R is H or a substituted or unsubstituted, branched or unbranched, cyclic or linear alkyl group. Examples include hydrogen peroxide, butyl hydroperoxide, ethylidene peroxide, ethyl hydroperoxide. In certain cases, the R could be sulfurous or phosphorus atoms (e.g. peroximonosulfuric acid).

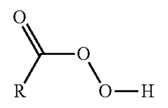

(III)

wherein R is a hydrogen, an oxygen, or a substituted or unsubstituted, branched or unbranched, cyclic or linear alkyl group. Examples include peroxycarboxylic acids (peracetic acid, peroctanoic acid, performic acid, peroxiphthalates, etc.), percarbonates (e.g. sodium percarbonates, potassium percarbonates), perbenzoic acid, cumene peroxide, and more.

Preferred peroxide compounds are hydrogen peroxide, sodium peroxide, benzoyl peroxide, dibenzyl peroxides, peroxycarboxylic acids (peracetic acid, peroctanoic acid, performic acid, etc.), percarbonates (e.g. sodium percarbonates, potassium percarbonates), peroxymonosulfuric acid, and peroxydisulfuric acid.

Cyclic Carbonates

When used herein, a cyclic carbonate is a compound according to Formula 1:

Formula 1

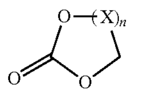

Wherein X=substituted or unsubstituted, branched, or unbranched alkyl group and wherein n is selected such that the compound is soluble enough in aqueous solutions to deliver its peroxide stability enhancing effects, with or without the use of solubility enhancing ingredients. For example, n may be from 0 to 16, 0 to 12, or 0 to 6.

One example is propylene carbonate:

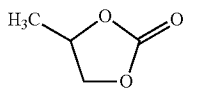

Other examples are trimethylene carbonate, ethylene carbonate, butylene carbonate, and glycerol carbonate.

Poly-Phosphonic Acid Chelating Agents and Salts Thereof and Certain Alkaline pH Adjusting Agents Other useful stabilizers disclosed in this invention are a combination of poly-phosphonic acid chelating agents, and salts thereof, and alkaline pH adjusting agents with a maximum pKb value of 3.0. Poly-phosphonic acid chelating agents are referred to chelating agents that contain more than one phosphonate or phosphonic acid group in each of their molecules. Examples of poly-phosphonic acid chelating agents are 1-hydroxyethane-1,1-diphosphonic acid (HEDP), aminotrimethylene phosphonic acid, di-ethylene tri-amine penta(methylene phosphonic acid), and ethylene di-amine tetra(methylene phosphonic acid), hexamethylenediamine-tetra(methylene phosphonic) acid. Examples of alkaline pH adjusting agents in accordance with the invention include potassium hydroxide (KOH), sodium hydroxide (NaOH), lithium hydroxide, magnesium hydroxide, calcium hydroxide, rubidium hydroxide, cesium hydroxide, strontium hydroxide and barium hydroxide.

Stabilizer Concentrations

The cyclic carbonates as stabilizers can be used in a concentration of from about 0.05, 1, 5, 10, or 15 wt. % or up to about 2.5, 7.5, 12.5, 17.5, 20, 30, 40 or 49 wt. %.

The w/w ratio of the poly-phosphonic acid chelating agent(s) and/or salt(s) thereof to the alkaline pH adjusting agent with a pKb value of up to 3.0 can be about 50:1, about 40:1, about 30:1, about 20:1, about 10:1, about 5:1, about 1:1, or about 1:5. Weight ratios in between these values are also contemplated herein.

Oxidizing Agents

In some embodiments, the compositions of the present invention may include from about 0.001 wt. % to about 99 wt. % of an oxidizing agent. In other embodiments, the compositions of the present invention may include from about 1 wt. % to about 60 wt. % of an oxidizing agent. In some other embodiments, the compositions of the invention may include from about 50 wt. % to about 80 wt. % of an oxidizing agent. In other embodiments, the compositions of the invention include about 15 wt. % to about 30 wt. % of an oxidizing agent. In still other embodiments, the compositions of the present invention include about 25 wt. % of an oxidizing agent. In further embodiments, the invention includes about 1 wt. % to about 20 wt. % of an oxidizing agent. It is to be understood that all ranges and values between these ranges and values are encompassed by the present invention. The skilled person will understand that certain oxidizing agents are also peroxide compounds.

Examples of inorganic oxidizing agents include the following types of compounds or sources of these compounds, or alkali metal salts of these types of compounds, or compounds forming an adduct therewith: hydrogen peroxide, urea-hydrogen peroxide complexes or hydrogen peroxide donors of: group 1 (IA) oxidizing agents, for example lithium peroxide, sodium peroxide; group 2 (IIA) oxidizing agents, for example magnesium peroxide, calcium peroxide, strontium peroxide, barium peroxide; group 12 (IIB) oxidizing agents, for example zinc peroxide; group 13 (IIIA) oxidizing agents, for example boron compounds, such as perborates, for example sodium perborate hexahydrate of the formula $Na_2[B_2(O_2MOH)_4]6H_2O$ (also called sodium perboratetetrahydrate); sodium peroxyborate tetrahydrate of the formula $Na_2B_2(O_2)_2$ $[(OH)_4].4H_2O$ (also called sodium perborate trihydrate); sodium peroxyborate of the formula $Na_2[B_2(O_2)_2(OH)_4]$ (also called sodium perborate monohydrate); group 14 (IVA) oxidizing agents, for example persilicates and peroxycarbonates, which are also called percarbonates, such as persilicates or peroxycarbonates of alkali metals; group 15 (VA) oxidizing agents, for example peroxynitrous acid and its salts; peroxyphosphoric acids and their salts, for example, perphosphates; group 16 (VIA) oxidizing agents, for example peroxysulfuric acids and their salts, such as peroxymonosulfuric and peroxydisulfuric acids, and their salts, such as persulfates, for example, sodium persulfate; and group Vila oxidizing agents such as sodium periodate, potassium perchlorate. Other active inorganic oxygen compounds can include transition metal peroxides; and other such peroxygen compounds, and mixtures thereof.

Examples of organic oxidizing agents include, but are not limited to, perbenzoic acid, derivatives of perbenzoic acid, t-butyl benzoyl hydroperoxide, benzoyl hydroperoxide, or any other organic based peroxide and mixtures thereof, as well as sources of these compounds. Other examples include, but are not limited to, peracids including C1-C12 percarboxylic acids such as peracetic acid, performic acid, percarbonic acid, peroctanoic acid, and the like; per-diacids or per-triacids such as peroxalic acid, persuccinic acid, percitric acid, perglycolic acid, permalic acid and the like; and aromatic peracids such as perbenzoic acid, or mixtures thereof.

In some embodiments, the compositions of the present invention employ one or more of the inorganic oxidizing agents listed above. Suitable inorganic oxidizing agents include ozone, hydrogen peroxide, hydrogen peroxide adduct, group IliA oxidizing agent, or hydrogen peroxide donors of group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Preferred oxidizing agents are hydrogen peroxide, and/or any inorganic or organic peroxide or peracid. In some embodiments, the oxidizing agent can also have antimicrobial activity. In other embodiments, the oxidizing agent is present in an amount insufficient to exhibit antimicrobial, bleaching or other activities known to a person skilled in the art.

Solvents or Carriers

The present inventive formulations may comprise solvents or carriers such as water, propylene glycol derivatives with ethoxylation and/or propoxylation, alkoxytriglycols and other glycols such as methoxytriglycol, ethoxytriglycol, butoxytriglycol, hexyltriglycol, propylene glycol methyl ether acetate, dipropylene glycol methyl ether acetate, dipropylene glycol n-butyl ether, propylene glycol n-butyl ether, dipropylene glycol n-propyl ether. Propylene glycol n-propyl ether, dipropylene glycol methyl ether, tripropylene glycol methyl ether, or mixtures thereof can be used. Other suitable solvents are benzyl alcohol, phenoxyethanol, phenethyl alcohol, methanol, ethanol, butyl 3-hydroxybutyrate, isopropyl alcohol, ethylhexylglycerol, branched or unbranched diols, charged or uncharged non-surfactant emulsifying agents, dibasic esters, polar protic solvents, polar aprotic solvents, and mixture thereof. When used, the solvent may be present in a concentration of from about 0.01, 0.05, 1, 5, 10, 15, 20, 30, 40, or 50 wt. % or up to about 25, 40, 60, 70, 85, or 99.9 wt. %. Preferably, the formulations comprise at least one solvent or carrier.

Carboxylic Acids

In some embodiments, the solutions or compositions may comprise at least one, branched or unbranched, saturated or unsaturated, substituted or unsubstituted, mono- or poly-carboxylic acid. The carboxylic acid may be chosen from C1 to C22 carboxylic acids. In some embodiments, the carboxylic acid may be a C5 to C11 carboxylic acid. In some embodiments, the carboxylic acid may be a C1 to C4 carboxylic acid. Examples of suitable carboxylic acids include but are not limited to furoic acid, salicylic acid, benzoic acid, citric acid, sulfosalicylic acid, sulfosuccinic acid, glycolic acid, lactic acid, formic acid, oxalic acid, malic acid, acetic acid, propionic acid, butanoic acid, pentanoic acid, hexanoic acid, heptanoic acid, octanoic acid, nonanoic acid, decanoic acid, undecanoic acid, dodecanoic acid, as well as their branched isomers, maleic acid, ascorbic acid, alpha-or-beta hydroxy-acetic acid, neopentanoic acid, neoheptanoic acid, neodecanoic acid, malonic acid, succinic acid, glutaric acid, adipic acid, pimelic suberic acid, and mixtures thereof.

When used, the acids may be present in a concentration of from about 0.05, 1, 10, or 20, wt. %, or up to 80, 60, 40, 30, 20, 10, or 5 wt. %.

Other Organic and Inorganic Acids

In certain embodiments, solutions or compositions may include one or more other organic acids, inorganic acids and salts thereof.

Suitable inorganic acids include but are not limited to sulfuric acid, sodium bisulfate, phosphoric acid, nitric acid, hydrochloric acid, hypochlorous acid, sulfamic acid, salts thereof, and mixtures thereof. Suitable organic acids include, but are not limited to, methane sulfonic acid, ethane sulfonic acid, propane sulfonic acid, butane sulfonic acid, xylene sulfonic acid, benzene sulfonic acid, toluenesulfonic acid, naphthalene disulfonic acid, alkyl sulfonic acids such as linear alkyl benzene sulphonic acid, alkyl diphenyloxide disulfonic acid, cumene sulfonic acid, xylene sulfonic acid, formic acid, acetic acid, glycolic acid, mono, di, or tri-halocarboyxlic acids, picolinic acid, dipicolinic acid, and mixtures thereof.

When present, the total amount of these organic and/or inorganic acids may be from about 0.01, 0.5, 1, 3, 10, 15 or 20 wt. % or less than about 60, 40, 20, 10, 3, or 1 wt. %.

Surfactants

The composition or solution of the invention may include any surfactant that is compatible with peroxides. The surfactants may be chosen from anionic, nonionic, amphoteric/zwitterionic and cationic surfactants, and mixtures thereof.

Exemplary nonionic, amphoteric, and zwitterionic surfactants are those disclosed in U.S. Pat. No. 8,871,807 to Gohl et al. (these surfactants are incorporated herein by reference). Suitable anionic surfactants include but are not limited to alkyl benzene sulfonic acid, alkyl diphenyloxide disulfonic acid, polyoxyethylene octyl ether carboxylic acid, C6-C22 alkyl sulfonic acid, xylenesulfonic acid, alkyl hydrogen sulfate, or alkyl phosphonic acids and salts thereof. Suitable cationic surfactants include but are not limited to linear alkyl-amines and alkyl-ammoniums such as benzalkonium chlorine, benzethonius chloride, distearyldimethylammonium chloride, and their non-salt forms.

When used, the surfactants may be present in a concentration of from about 0.01, 0.5, 5, 15, 20 or 40 wt. %, or less than about 70, 50, 25, 10, 3, or 1 wt. %.

Hydrotropes

The composition or solution of the invention may include one or more hydrotropes. The hydrotropes include but are not limited to xylene sulfonic acid, cumene sulfonic acid, toluene sulfonic acid and their salts, polyether phosphate esters, diphenyloxide disulfonates, and benzoic acid salts.

When used, the hydrotrope may be present in an amount from about 0.01, 1, 3, 5, 10, or 20 wt. % or up to about 25, 15, 8, 4, 1.5, or 0.1 wt. %.

Antimicrobial Compounds

In other embodiments, the compositions may include an antimicrobial compound (e.g. sanitizing or disinfecting agent) for killing microbes and the like. The antimicrobial compound may be chosen from and is not limited to essential oils, quaternary ammonium compounds, organic acids, parabens, aldehydes, phenolic compounds, alcohols, halogen-type or peroxygen-type bleaches, formaldehyde or formaldehyde releasing agents, peroxy-carboxylic acids, or mixtures thereof.

When used, the concentration of the antimicrobial compound may be from about 0.005, 0.1, 1, 5, 10, 20, 40, or 60 wt. %, or up to about 50, 30, 15, 3, or 0.5 wt. %.

Cyclic Alcohols

Some embodiments may include a cyclic alcohol. The cyclic alcohol may be chosen from and is not limited to benzyl alcohol, phenoxyethanol, and phenethyl alcohol. When used, the cyclic alcohol can be present in a concentration of from about 0.02, 0.5, 2, 5, 10, 15, 20, or 25 wt. % or up to about 60, 50, 40, 30, 20, 10, or 5 wt. %.

Additional Ingredients

The present inventive compositions may include additional ingredients as would be apparent to the person skilled in the art, including without limitation, pigments and dyes, fragrances, rheology modifiers, corrosion inhibitors, anti-foaming agents, skin conditioning agents, softening agents, anti-static agents, anti-wrinkling agents, dye transfer inhibition/color protection agents, odor removal/odor capturing agents buffers, pH adjusting agents, builders, emollients, bleach activators, enzymes, chelating agents, brighteners, radical scavengers, preservatives, soil shielding/soil releasing agents, ultraviolet light protection agents, water repellency agents, insect repellency agents, anti-pilling agents, souring agents, mildew removing agents, allergicide agents, and mixtures thereof.

When used, one or more dyes may be present in a concentration of from about 0.0002, 0.05, 1, 2, or 3 or up to about 5, 3, 2, 1, 0.5 or 0.01 wt. %.

Fragrances may be present in a concentration of from about 0.01, 0.5, 1, or 5 wt. % or up to about 7, 3, 2, 0.2 wt. %.

Rheology modifiers, including but not limited to xanthan gum or guar gum, may be present in a concentration of from about 0.02, 0.5, 1, 5, 10 wt. %, or up to about 15, 7, 3, 0.7, 0.1, or 0.02 wt. %.

Corrosion inhibitors, including but not limited to benzotriazoles, molybdate salts, zinc dithiophosphate, may be present in a concentration of from about 0.01, 0.5, 1, 5, 10 wt. %, or up to about 15, 7, 3, 0.1, 0.05 wt. %.

Anti-foaming agents, including but not limited to siloxanes, low-solubility oils, low-HLB nonionic surfactants, may be present in a concentration of from about 0.001, 0.1, 0.5, 2, 4, 5, or 7 wt. %, or up to about 10, 8, 5, 4, or 3 wt. %.

Buffering agents may be present in a concentration of from about 0.01, 0.5, 1, 5, or 7 wt. %, or up to about 10, 5, 3, 0.1, or 0.05 wt. %.

Emollients or skin conditioning agents, such as glycerin, glycerides, lanolin, long chain fatty acids, long chain alcohols, and phospholipids, may be present in a concentration of from about 0.01, 0.5, 2, 5, or 10 wt. %, or up to about 15, 8, 4, 1, or 0.1 wt. %.

Builders may be present in a concentration of from about 0.01, 0.5, 2, 4, or 8 wt. %, or up to about 5, 3, 1, or 0.1 wt. %.

Bleach activators may be present in a concentration of from about 0.0005, 0.01, 1, 5, or 10 wt. %, or up to about 15, 8, 3, or 0.1 wt. %.

Soil suspenders may be present in a concentration of from about 0.01, 0.5, 2, 5, or 10 wt. %, or up to about 15, 8, 4, 1, or 0.1 wt. %.

Brighteners may be present in a concentration of from about 0.0005, 0.05, 0.1, 2, or 7 wt. %, or up to about 10, 5, 3, 1, or 0.01 wt. %.

Radical scavengers may be present in a concentration of from about 0.005, 0.5, 1, 5, or 15 wt. %, or up to about 20, 10, 3, 0.1, or 0.01 wt. %.

Compositions or solutions according to the invention can be formulated in concentrated or solid form (e.g. tablets, powder, etc.), as well as in multi-part systems such as two-part systems wherein liquid components are included in one part, and solid components are included in another part. Solutions according to the invention can be packaged in a dispenser, such as a spray dispenser, or another suitable dispenser package.

Embodiments of the invention can be used for a variety of purposes, such as in cleaning, disinfection and antisepsis, topical treatments, bleaching, water and soil treatment, petroleum extraction and refinery, polymer chemistry, mining, catalytic reactions, pollutant destruction, dechlorination, odor control and air treatment, peracid formation, and food processing applications.

The following examples will help to illustrate the utility and novelty of the invention.

Test Results

Accelerated aging tests were used to determine the stability of peroxide formulations disclosed herein. Accelerated aging tests involve incubation of the aforementioned peroxide containing formulations in chambers with elevated temperatures of 40° C., 50° C. or 54° C. for a set period of time and then testing the final peroxide concentrations using an optimized iodine-based titration method and comparing them to each formulation's initial peroxide concentration that was measured prior to the accelerated aging tests. In accelerated aging conditions at elevated temperatures, the reactions that possibly lead to degradation of peroxide compounds in solution are thermodynamically accelerated and therefore this method replaces the need to wait for much longer periods of incubation time at ambiant temperatures to see whether the peroxide compounds are stable in the prepared formulations. The iodometric titration has a sum marginal error range of about +1-0.05%.

Ingredient List

The ingredients used in the solutions tested and set forth before are summarized as follows:

Peroxide Compound/Oxidizing Agent

Hydrogen Peroxide—an aqueous stock of 50 wt. % technical grade hydrogen peroxide, sourced from Arkema Inc.

Cyclic Carbonates

Propylene Carbonate—99.7 wt. % stock sourced from Sigma Aldrich

Glycerol Carbonate—99 wt. % stock manufactured by Huntsman International; trade name: Jeffsol® GC Ethylene Carbonate—98 wt. % stock sourced from Sigma Aldrich Alkaline pH Adjusting Agents with a Maximum pKb Value of 3.0

Potassium hydroxide (KOH)—an aqueous stock solution of 45 wt. % potassium hydroxide in deionized water available as a commodity chemical ingredient from multiple sources.

Sodium hydroxide (NaOH—an aqueous stock solution of 10 wt. % sodium hydroxide in deionized water available as a commodity chemical ingredient from multiple sources.

Poly-Phosphonic Acid Chelating Agents

Dequest 2010-60 wt. % aqueous stock of etidronic acid, manufactured by Italmatch Chemicals Other Chelating Agents Trilon M Liquid—a 40 wt. % aqueous stock of methyiglycinediacetic acid trisodium salt, manufactured by BASF Dissolvine GL-47-S—a 47-49 wt. % L-glutamic acid, N,N-diacetic acid tetrasodium salt, manufactured by AkzoNobel Inc.

Surfactants

Bio-terge PAS-8S—38 wt. % aqueous stock of sodium octanesulfonate, manufactured by Stepan Company Bio-soft S-101-90—100 wt. % (examples below used 95.5 wt. %) aqueous stock of dodecyl benzene sulfonic acid (DDBSA), manufactured by Stepan Company Pluronic L62—100 wt. % stock of methyl-oxirane block copolymer with oxirane, manufactured by BASF Tomadol 91-2.5 and Tomadol 91-6—100 wt. % stock of ethoxylated C9-C11 alcohols, manufactured by Air Products Glucopon 600 UP—50 wt. % aqueous stock of oligomeric D-glucopyranose C10-C16-alkyl glucosides, manufactured by BASF Pluronic 17R4—a 100 wt. % methyl-oxirane polymer with oxirane, manufactured by BASF Inc.

Solvent

Dowanol TPM and Dowanol DPM—100 wt. % stocks of tripropylene glycol methyl ether and dipropylene glycol methyl respectively, manufactured by Dow Chemicals Omnia Solvent—a .gtoreq.98 wt. % butyl-3-hydroxybutyrate, manufactured by Eastman Chemicals Benzyl alcohol—95 wt. % stock, manufactured by INEOS Acidifiers Lutropur MSA 100—a 99.5 wt. % stock of methanesulfonic acid, manufactured by BASF Benzenesulfonic acid—90 wt. % stock, sourced from Sigma Aldrich p-toluenesuffonic acid monohydrate—98.5 wt. % stock, sourced from Sigma Aldrich Salicylic Acid—100 wt. % stock, sourced from Sigma Aldrich 2-Furolc acid—100 wt. % stock, manufactured by PennAKem Citric acid—95 wt. % stock, manufactured by Jungbunzlauer Benzoic acid—95 wt. % stock, manufactured by Emerald Performance Materials Corrosion Inhibitor Cobratec 35G—35 wt. % solution of benzotriazole in propylene glycol, manufactured by PMC Specialties Group Defoamer Antifoam XFO-64, a proprietary defoaming agent, available from Ivanhoe Industries Inc.

Fragrance

Spring Fresh Fragrance, a proprietary fragrance manufactured by Robertet Inc.

The below tables recite the amounts of the above ingredients employed.

Where such ingredients are not present in "pure" form (i.e. 100 wt. % concentration of the compound), actual concentrations in the test solutions will be less than as stated and can be calculated by multiplying the above stated concentrations by the concentrations recited in the below tables. For example, solution 1 contains 10 wt. % propylene carbonate present as a 99.7 wt. % stock solution. Therefore, the ACTUAL amount of propylene carbonate in solution 1 is 10×0.997=9.97 wt. %.

The pH values for solutions in tables 2 to 8, containing methane sulfonic acid or another sulfonic acids, is about 0.

Example 1

Tests were performed to determine the effect of two different carbonates on the stability of hydrogen peroxide solutions at different pH ranges (mildly acidic and mildly alkaline) and for different storage times and storage temperatures. The results are summarized in Table 1 below.

TABLE 1

| Solution Ingredients | #1 | #2 | #3 | #4 | #5 |
|---|---|---|---|---|---|
| | Amount (wt. %) | | | | |
| Hydrogen peroxide (initial amount) | 15.6 | | | 6 | |
| KOH | pH to 8.5 | | | pH to 4.0 | |
| Glycerol Carbonate | 0 | 10 | 0 | 0 | |
| Propylene Carbonate | 10 | 0 | 0 | 3.5 | 0 |
| % Peroxide Loss** (54° C., 2 weeks) | 3.83 | 1.88 | 100 | 1.75 | 3.0 |
| % Peroxide Loss** (40° C., 1 month) | 1.06 | 0.46 | 95.75 | Not tested | Not tested |
| Peroxide Stability Improvement at 54° C. incubation (%)*** | 96.2% vs. #3 | 98.1% vs. #3 | — | 42% vs. #5 | — |
| Peroxide Stability Improvement at 40° C. incubation (%)*** | 98.9% vs. #3 | 99.5% vs. #3 | — | — | — |

**% Peroxide loss was calculated as follows:

$$\% \text{ Peroxide loss} = \frac{(\text{starting H2O2 concentration} - \text{final H2O2 concentration})}{\text{starting H2O2 concentration}} \times 100$$

***Peroxide Stability Improvement (%) was calculated by comparing the % peroxide loss from the formulation(s) containing the disclosed inventive peroxide stabilizer(s), versus the same formulations without those stabilizer(s) and converting to a percentile value.

In Table 1, KOH was used in each solution to adjust the pH to the values shown above. The balance of each solution was deionized water.

Solutions #1 and #2 contained 10 wt. % propylene carbonate and glycerol carbonate, respectively. Solution #3 contained no cyclic carbonates. The peroxide loss of Solution #3 was 100% when the solution was stored at 54.degree. C. for 2 weeks as compared to only 3.83% and 1.88% peroxide loss for Solutions #1 and #2, respectively. Solution #4 contained 3.5 wt. % propylene carbonate. Solution #5 contained no carbonates. The peroxide loss over a 2 week period at 54.degree. C. was 1.75% for Solution #4 as compared to 3.0% for Solution #5. Thus, Solution #1 exhibited a 98.9% stability improvement relative to Solution #3. Solution #2 exhibited a 99.5% stability improvement over solution #3. Solution #4 exhibited a 42% stability improvement over solution #5.

Example 2

Tests were performed to determine the effect of adding 10 wt. % propylene carbonate to various concentrated hydrogen peroxide-based disinfectant solutions (Solutions #6-#17). The results are summarized in Tables 2a and 2b below.

TABLE 2a

| | Solution | | | | | |
|---|---|---|---|---|---|---|
| Ingredients | #6 | #7 | #8 | #9 | #10 | #11 |
| | Amount (wt. %) | | | | | |
| Bio-soft S-101 | 17.5 | 17.5 | 14 | 14 | 17.5 | 17.5 |
| Pluronic L62 | 3 | 3 | 3 | 3 | 3 | 3 |
| Tomadol 91-2.5 | 1 | 1 | 1 | 1 | 1 | 1 |
| Tomadol 91-6 | 1 | 1 | 1 | 1 | 1 | 11 |
| Dowanol TPM | 13.5 | 13.5 | 13.5 | 13.5 | 11 | 11 |

TABLE 2a-continued

| Ingredients | Solution #6 | #7 | #8 | #9 | #10 | #11 |
|---|---|---|---|---|---|---|
| | Amount (wt. %) | | | | | |
| Salicylic acid | 3.3 | 3.3 | 3.3 | 3.3 | 2 | 2 |
| Lutropur MSA 100 | 3.05 | 3.05 | 3.05 | 3.05 | 3.05 | 3.05 |
| KOH | 0.2 | 0.2 | 0.2 | 0.2 | 0.2 | 0.2 |
| Hydrogen peroxide | 15.2 | 15.2 | 15.2 | 15.2 | 15.2 | 15.2 |
| Propylene Carbonate | 0 | 10 | 0 | 10 | 0 | 10 |
| % Peroxide Loss (54° C., 2 weeks) | 2.97 | 0.212 | 3.80 | 1.05 | 2.70 | 1.18 |
| Peroxide Stability Improvement (%) | 92.9% | | 72.4% | | 56.3% | |

TABLE 2b

| Ingredient | Solution #12 | #13 | #14 | #15 | #16 | #17 |
|---|---|---|---|---|---|---|
| | Amount (wt. %) | | | | | |
| Bio-soft S-101 | 17.5 | 17.5 | 17.5 | 17.5 | 14 | 14 |
| Pluronic L62 | 3 | 3 | 1.5 | 1.5 | 1.5 | 1.5 |
| Tomadol 91-2.5 | 1 | 1 | 0.5 | 0.5 | 0.5 | 0.5 |
| Tomadol 91-6 | 1 | 1 | 0.5 | 0.5 | 0.5 | 0.5 |
| Dowanol TPM | 13.5 | 13.5 | 13.5 | 13.5 | 12 | 12 |
| Salicylic acid | 3.3 | 3.3 | 3.3 | 3.3 | 2 | 2 |
| Lutropur MSA 100 | 3.05 | 3.05 | 3.05 | 3.05 | 2.3 | 2.3 |

TABLE 2b-continued

| Ingredient | Solution #12 | #13 | #14 | #15 | #16 | #17 |
|---|---|---|---|---|---|---|
| | Amount (wt. %) | | | | | |
| Dequest 2010 | 0.5 | 0.5 | 1 | 1 | 0.5 | 0.5 |
| KOH | 0.1 | 0.1 | 0.2 | 0.2 | 0.1 | 0.1 |
| Hydrogen peroxide | 15.2 | 15.2 | 15.2 | 15.2 | 15.2 | 15.2 |
| Propylene Carbonate | 0 | 10 | 0 | 10 | 0 | 10 |
| % Peroxide Loss (54° C., 2 weeks) | 5.76 | 4.79 | 6.48 | 3.37 | 2.61 | 0.00 |
| Peroxide Stability Improvement (%) | 16.8% | | 48.0% | | 100% | |

Solutions #6 to #17 demonstrate that the addition of propylene carbonate improved peroxide stability of the solutions over an accelerated aging period, regardless of the rest of the Ingredients that were included in the formulations.

Example 3

Tests were performed to determine the effect of adding different amounts of propylene carbonate to various test solutions. The results are summarized in Tables 3a and 3b below.

TABLE 3a

| Ingredients | #18 | #19 | #20 | #21 | #22 | #23 | #24 | #25 | #26 | #27 | #28 |
|---|---|---|---|---|---|---|---|---|---|---|---|
| | | | | | Amount (wt. %) | | | | | | |
| Biosoft S-101 | | | | | | 17.5 | | | | | |
| Pluronic L62 | | | | | | 3 | | | | | |
| Tomadol 91-2.5 | | | | | | 1 | | | | | |
| Tomadol 91-6 | | | | | | 1 | | | | | |
| Hydrogen peroxide | | | | | | 15.2 | | | | | |
| Dowanol TPM | | | | | | 17.25 | | | | | |
| Salicylic acid | | | | | | 4 | | | | | |
| Dequest 2010 | | | | | | 0.7 | | | | | |
| KOH | | | | | | 0.14 | | | | | |
| Propylene carbonate | 0.5 | 1 | 2 | 5 | 0.5 | 1 | 2 | 5 | 1 | 5 | 10 |
| Benzensulfonic acid | | 3.4 | | | | | | 0 | | | |
| p-Toluenesulfonic acid monohydrate | | 0 | | | | 3.4 | | | | 0 | |
| % Peroxide Loss (54° C., 2 Weeks) | 4.71 | 4.12 | 4.1 | 3.71 | 4.52 | 3.69 | 3.39 | 2.67 | 3.03 | 1.75 | 0.22 |
| Peroxide Stability Improvement (%) | — | 12.53 vs. #18 | 12.95 vs. #18 | 21.23 vs. #18 | — | 18.36 vs. #22 | 25.00 vs. #22 | 40.93 vs. #22 | — | 42.24 vs. #26 | 92.74 vs. #26 |

TABLE 3b

| Ingredient | Solution #29 | #30 | #31 | #32 | #33 | #34 | #35 |
|---|---|---|---|---|---|---|---|
| | Amount (wt. %) | | | | | | |
| Bio-soft S-101 | 17.5 | 17.5 | 17.5 | 17.5 | 17.5 | 17.5 | 17.5 |
| Pluronic L62 | 3 | 3 | 3 | 3 | 3 | 3 | 3 |
| Tomadol 91-2.5 | 1 | 1 | 1 | 1 | 1 | 1 | 1 |
| Tomadol 91-6 | 1 | 1 | 1 | 1 | 1 | 1 | 1 |
| Dowanol TPM | 13.5 | 13.5 | 13.5 | 13.5 | 13.5 | 13.5 | 13.5 |
| Salicylic acid | 3.3 | 3.3 | 3.3 | 3.3 | 3.3 | 3.3 | 3.3 |
| Lutropur MSA 100 | 3.05 | 3.05 | 3.05 | 3.05 | 3.05 | 3.05 | 3.05 |
| Dequest 2010 | 1 | 1 | 1 | 1 | 1 | 1 | 1 |
| KOH | 0.2 | 0.2 | 0.2 | 0.2 | 0.2 | 0.2 | 0.2 |
| Hydrogen peroxide | 15.2 | 15.2 | 15.2 | 15.2 | 15.2 | 15.2 | 15.2 |
| Propylene Carbonate | 0 | 2.5 | 5 | 7.5 | 10 | 12.5 | 17.5 |
| % Peroxide Loss (54° C., 2 weeks) | 1.35 | 0.41 | 0 | 0 | 0 | 0 | 0 |
| Peroxide Stability Improvement (%) | — | 69.6% vs. #29 | 100% vs. #29 | 100% vs. #29 | 100% vs. #29 | 100% vs. #29 | 100% vs. #29 |

As shown in Tables 3a and 3b, the peroxide loss decreased as the concentration of propylene carbonate was increased.

Example 4

Tests were performed to assess the effect of increasing the peroxide concentration in a base formula, with or without 10 wt. % propylene carbonate. The results are shown in Tables 4a and 4b below and plotted in FIG. 1.

TABLE 4a

| Ingredient | Solution #36 | #37 | #38 | #39 | #40 | #41 |
|---|---|---|---|---|---|---|
| | Amount (wt. %) | | | | | |
| Biosoft S-101 | 17.5 | 17.5 | 17.5 | 17.5 | 17.5 | 17.5 |
| Pluronic L62 | 3 | 3 | 3 | 3 | 3 | 3 |
| Tomadol 91-2.5 | 1 | 1 | 1 | 1 | 1 | 1 |
| Tomadol 91-6 | 1 | 1 | 1 | 1 | 1 | 1 |
| Dowanol TPM | 13.5 | 13.5 | 13.5 | 13.5 | 13.5 | 13.5 |
| Salicylic acid | 3.3 | 3.3 | 3.3 | 3.3 | 3.3 | 3.3 |
| Lutropur MSA 100 | 3.05 | 3.05 | 3.05 | 3.05 | 3.05 | 3.05 |
| Dequest 2010 | 1 | 1 | 1 | 1 | 1 | 1 |
| KOH | 0.2 | 0.2 | 0.2 | 0.2 | 0.2 | 0.2 |
| Cobratec 35G | 0.2 | 0.2 | 0.2 | 0.2 | 0.2 | 0.2 |
| Hydrogen peroxide | 8 | 8 | 10 | 10 | 13 | 13 |
| Propylene Carbonate | 0 | 10 | 0 | 10 | 0 | 10 |
| % Peroxide Loss (54° C., 2 weeks) | 2.12 | 0 | 2.01 | 0 | 0.61 | 0 |
| Peroxide Stability Improvement (%) | 100% | | 100% | | 100% | |

TABLE 4b

| Ingredient | Solution #42 | #43 | #44 | #45 |
|---|---|---|---|---|
| | Amount (wt. %) | | | |
| Bio-soft S-101 | 17.5 | 17.5 | 17.5 | 17.5 |
| Pluronic L62 | 3 | 3 | 3 | 3 |
| Tomadol 91-2.5 | 1 | 1 | 1 | 1 |
| Tomadol 91-6 | 1 | 1 | 1 | 1 |
| Dowanol TPM | 13.5 | 13.5 | 13.5 | 13.5 |
| Salicylic acid | 3.3 | 3.3 | 3.3 | 3.3 |
| Lutropur MSA 100 | 3.05 | 3.05 | 3.05 | 3.05 |
| Dequest 2010 | 1 | 1 | 1 | 1 |
| KOH | 0.2 | 0.2 | 0.2 | 0.2 |
| Cobratec 35-G | 0.2 | 0.2 | 0.2 | 0.2 |
| Hydrogen peroxide | 18 | 18 | 22 | 22 |
| Propylene Carbonate | 10 | 0 | 10 | 0 |
| % Peroxide Loss (54 C., 2 weeks) | 0.42 | 0 | 2.03 | 0 |
| Peroxide Stability Improvement | 100% | | 100% | |

Example 5

Tests were performed to determine the effect of other carbonate compounds, namely, ethylene carbonate and glycerol carbonate, on hydrogen peroxide stability. The results are shown in Table 5 below.

TABLE 5

| Ingredient | Solution #46 | #47 | #48 |
|---|---|---|---|
| | Amount (wt. %) | | |
| Bio-soft S-101 | 17.5 | 17.5 | 17.5 |
| Pluronic L62 | 3 | 3 | 3 |
| Tomadol 91-2.5 | 1 | 1 | 1 |
| Tomadol 91-6 | 1 | 1 | 1 |
| Dowanol TPM | 13.5 | 13.5 | 13.5 |
| Salicylic acid | 3.3 | 3.3 | 3.3 |
| Lutropur MSA 100 | 3.05 | 3.05 | 3.05 |
| Dequest 2010 | 1 | 1 | 1 |
| KOH | 0.2 | 0.2 | 0.2 |
| Hydrogen peroxide | 10 | 10 | 10 |
| Ethylene Carbonate | 0 | 5 | 0 |
| Glycerol Carbonate | 0 | 0 | 5 |
| % Peroxide Loss (54° C.; 2 weeks) | 3.73 | 1.03 | 1.94 |
| Peroxide Stability Improvement (%) | — | 72.4% vs. #46 | 48% vs. #46 |

The above results show that these other carbonate compounds are also effective in stabilizing hydrogen peroxide solutions.

Example 6

Further tests were done to determine the effect of propylene carbonate on the stability and microbicidal efficacy of a ready-to-use (RTU) peroxide based disinfectant solution. The results are shown below in Table 6.

TABLE 6

| Ingredient | Solution #49 | #50 |
|---|---|---|
| | Amount (wt. %) | |
| Glucopon 600 UP | 0.2 | 0.2 |
| Bio-soft S-101 | 0.25 | 0.25 |

TABLE 6-continued

| Ingredient | Solution #49 | #50 |
|---|---|---|
| | Amount (wt. %) | |
| Bio-terge PAS-8S | 0.2 | 0.2 |
| 2-Furoic Acid | 0.5 | 0.5 |
| Salicylic acid | 0.12 | 0.12 |
| Trilon M Liquid | 0.1 | 0.1 |
| Propylene Carbonate | 0 | 2.5 |
| Hydrogen peroxide | 0.5 | 0.5 |
| % Peroxide Loss (54° C., 2 weeks) | 1.95 | 1.31 |
| Log Reduction (*S. aureus*) | 4.3 | 5.3 |

Microbicidal efficacy was conducted using the ASTM E2197-02 Standard Quantitative Disk Carrier Test (QCT-2) method, in the presence of 5 wt. % organic soil challenge and 2 minutes of exposure (contact time). As shown above, the stability of a ready-to-use peroxide disinfectant solution can also be enhanced by the addition of propylene carbonate. The microbicidal efficacy is also increased by 1 log following the addition of propylene carbonate.

Example 7

Still further tests were done to assess the effect of adding low amounts of editronic acid (also called HEDP or Dequest 2010) (up to 1 wt. %) to the stability of concentrated hydrogen peroxide solutions with or without alkali metal hydroxides (NaOH and KOH). The results are shown in Table 7 below.

TABLE 7

| Ingredient | Solution #51 | #52 | #53 | #54 | #55 | #56 |
|---|---|---|---|---|---|---|
| | Amount (wt. %) | | | | | |
| Bio-soft S-101 | 18 | 18 | 18 | 18 | 18 | 18 |
| Dowanol DPM | 17 | 17 | 17 | 17 | 17 | 17 |
| Lutropur MSA 100 | 3 | 3 | 3 | 3 | 3 | 3 |
| Salicylic acid | 3.3 | 3.3 | 3.3 | 3.3 | 3.3 | 3.3 |
| Pluronic L62 | 3 | 3 | 3 | 3 | 3 | 3 |
| Hydrogen peroxide | 15 | 15 | 15 | 15 | 15 | 15 |
| Dequest 2010 | 0 | 0.5 | 0.5 | 1 | 1 | 1 |
| KOH | 0 | 0 | 0.1 | 0 | 0.2 | 0 |
| NaOH | 0 | 0 | 0 | 0 | 0 | 1 |
| % Peroxide Loss (54° C., 2 weeks) | 8.86 | 4.31 | 2.31 | 3.66 | 3.02 | 3.43 |
| Peroxide Stability Improvement (%) | — | 51.4% vs. #51 | 73.9% vs. #51 | 15% vs. #51 | 30% vs. #51 | 30.4% vs. #51 |

These results show that adding a low amount of HEDP will improve the stability of concentrated hydrogen peroxide solutions (compare solution #52 with solution #51). The further addition of an alkali metal hydroxide (KOH, NaOH) further enhances the stabilizing effect (see solutions #53, #54, #55, and #56). This result is unexpected because hydrogen peroxide is known to be less stable at alkaline pH values and both KOH and NaOH are alkaline pH adjusting agents with a pKb value up to or less than 3.0.

Example 8

Figure 2:
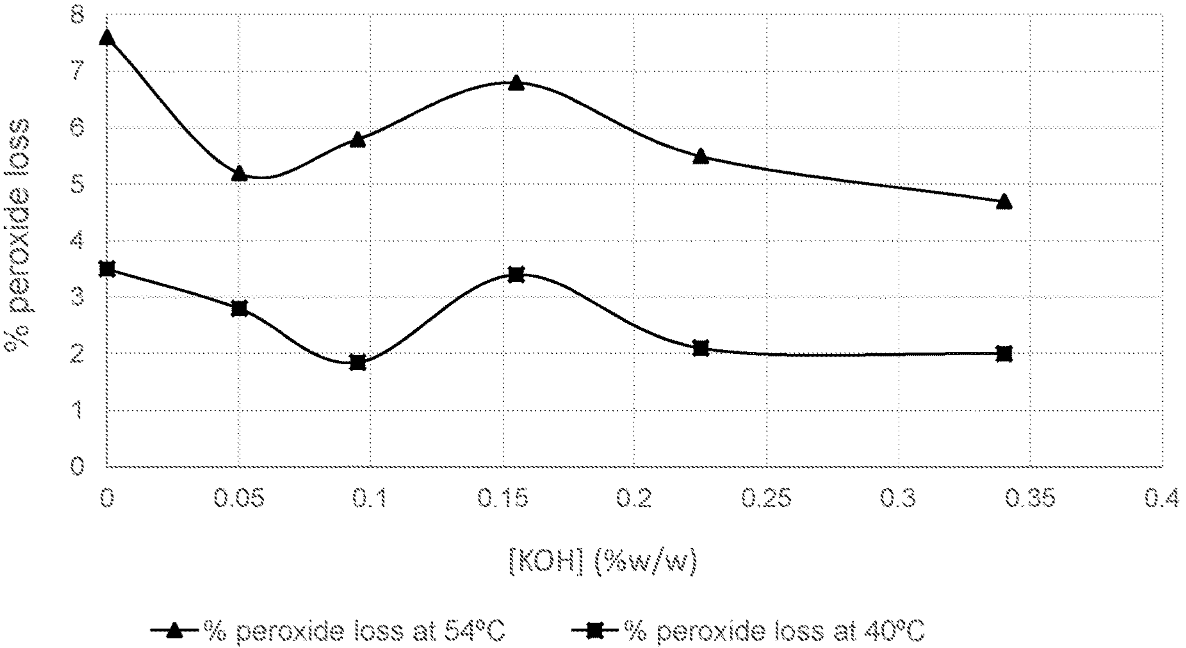
FIG. 2 is a graph showing the effect of varying amounts of KOH together with a fixed amount of HEDP (1 wt. %) on peroxide loss.

Tests were conducted to demonstrate the effect of increasing amounts of KOH on the overall peroxide stability, when the concentration of HEDP is kept constant at 1 wt. %. The results are shown below in Table 8 and plotted in FIG. 2.

TABLE 8

| Ingredient | Solution #57 | #58 | #59 | #60 | #61 | #62 |
|---|---|---|---|---|---|---|
| | Amount (wt. %) | | | | | |
| Bio-soft S-101 | 18 | 18 | 18 | 18 | 18 | 18 |
| Dowanol DPM | 17 | 17 | 17 | 17 | 17 | 17 |
| Lutropur MSA 100 | 3 | 3 | 3 | 3 | 3 | 3 |
| Salicylic acid | 3.3 | 3.3 | 3.3 | 3.3 | 3.3 | 3.3 |
| Pluronic L62 | 3 | 3 | 3 | 3 | 3 | 3 |
| Hydrogen peroxide | 15 | 15 | 15 | 15 | 15 | 15 |
| Dequest 2010 | 1 | 1 | 1 | 1 | 1 | 1 |
| KOH | 0 | 0.1 | 0.2 | 0.35 | 0.5 | 0.75 |
| % Peroxide Loss (54° C., 2 weeks) | 7.54 | 5.35 | 5.89 | 6.57 | 5.48 | 4.54 |
| % Peroxide Loss (40° C., 1 month) | 3.42 | 2.68 | 1.69 | 3.22 | 2.06 | 1.94 |
| Peroxide Stability Improvement (%) | — | 21.6% vs. #57 | 50.5% vs. #57 | 5.8% vs. #57 | 39.7% vs. #57 | 43.3% vs. #57 |

The above results show that increasing the concentration of KOH while keeping the Dequest 2010 concentration constant at 1 wt. %, leads to an improvement in the peroxide stability no matter how much KOH is added. The graph shows that at about 0.15 wt. % KOH, the combination has the lowest ability to improve peroxide stability, meanwhile at KOH concentrations above and below about 0.15 wt. % the peroxide stabilization effect in the system is maximized.

Additional Embodiments

Additional embodiments of the invention are disclosed below.

TABLE 9

Solution 63 is an example floor sanitizer.

| Ingredient | Solution #63 Amount (wt. %) |
|---|---|
| Glucopon 600 UP | 0.08 |
| Bioterge PAS-8S | 0.12 |
| Salicylic acid | 0.10 |
| Citric acid | 0.05 |
| Benzyl alcohol | 0.50 |
| Furoic acid | 0.10 |
| Lutropur MSA 100 | 0.04 |
| Triton M | 0.05 |
| Hydrogen peroxide | 3.00 |
| Spring Fresh Fragrance | 0.05 |
| Propylene Carbonate | 2.50 |
| Antifoam XFO 64 | 0.02 |
| pH | 2.0 |

TABLE 10

Solution 64 is an example pet shampoo.

| Ingredient | Solution #64 Amount (Wt. %) |
|---|---|
| Biosoft S-101 | 0.45 |
| Bioterge PAS-8S | 0.75 |
| Pluronic 17R4 | 0.9 |
| Propylene Carbonate | 2.5 |
| Omnia Solvent | 0.2 |
| Benzoic acid | 0.2 |
| Citric acid | 0.2 |

TABLE 10-continued

Solution 64 is an example pet shampoo.

| Ingredient | Solution #64 Amount (Wt. %) |
|---|---|
| Hydrogen peroxide | 2.4 |
| Dissolvine GL-47-S | 0.17 |
| KOH | pH to 5.5 |

It will be appreciated that variations to the above described embodiments can be made without departing from the scope of the invention herein described and claimed.

I claim:

1. A method of stabilizing a peroxide compound in a solution comprising adding to the solution an effective amount of poly-phosphonic acid chelating agents or salts thereof, and alkaline pH adjusting agents with a pKb value of up to 3.0, wherein the w/w ratio of the poly-phosphonic acid chelating agent or salt thereof to the alkaline pH adjusting agent is from about 1:1 to about 100:1, and wherein the pH of the solution is from about 0.1 to 2;

wherein combinations of the poly-phosphonic acid chelating agents or salts thereof and the alkaline pH adjusting agents with a pkb value of up to 3.0 are peroxide stabilizing agents, wherein the solution optionally comprises cyclic carbonates as peroxide stabilizing agents, and wherein the solution is free of additional peroxide stabilizing agents.

2. The method of claim 1, wherein the solution is free of quaternary ammonium compounds.

3. The method of claim 1, wherein the peroxide compound is selected from the group comprising hydrogen peroxide, percarbonate, perborate, persulfate, perphosphate, peroxymonosulfuric acid, peroxycarboxylic acids, or mixtures thereof.

4. The method of claim 1, wherein the poly-phosphonic acid chelating agent or salt thereof comprises 1-hydroxyethane-1,1-diphosphonic acid (HEDP), aminotrimethylene phosphonic acid, di-ethylene tri-amine penta (methylene phosphonic acid), ethylene di-amine tetra(methylene phosphonic acid), hexamethylenediamine-tetra(methylene phosphonic) acid, salts thereof, or any mixture thereof.

5. The method of claim 4, wherein the poly-phosphonic acid chelating agent is 1-hydroxyethane-1,1-diphosphonic acid (HEDP).

6. The method of claim 1, wherein the alkaline pH adjusting agent with a pKb value of up to 3.0 comprises potassium hydroxide (KOH), sodium hydroxide (NaOH), lithium hydroxide, magnesium hydroxide, calcium hydroxide, rubidium hydroxide, cesium hydroxide, strontium hydroxide, barium hydroxide, or any mixture thereof.

7. The method of claim 6, wherein the alkaline pH adjusting agent with a pKb value of up to 3.0 comprises potassium hydroxide, sodium hydroxide, or any mixture thereof.

8. The method of claim 1, wherein the w/w ratio of the poly-phosphonic acid chelating agent or salt thereof to alkaline pH adjusting agent with a pKb value of up to 3.0 is from about 1:1 to about 20:1.

9. The method of claim 1, wherein the ratio of the poly-phosphonic acid chelating agent or salt thereof to alkaline pH adjusting agent with a pKb value of up to 3.0 is about 10:1.

10. The method of claim 1, wherein the peroxide compound is present in a concentration of from about 0.05 wt. % to about 49 wt. % in the solution.

11. The method of claim 1, wherein the poly-phosphonic acid chelating agent or salt thereof is 1-hydroxyethane-1,1-diphosphonic acid (HEDP), and wherein the alkaline pH adjusting agent with a pKb value of up to 3.0 is potassium hydroxide.

12. The method of claim 1, wherein the solution further comprises an anionic surfactant selected from alkyl benzene sulfonic acid, alkyl diphenyloxide disulfonic acid, polyoxyethylene octyl ether carboxylic acid, C6-C22 alkyl sulfonic acid, xylene sulfonic acid, alkyl hydrogen sulfate, or alkyl phosphonic acids or salts thereof.

13. The method of claim 12, wherein the anionic surfactant is selected from an alkyl benzene sulfonic acid, alkyl diphenyloxide disulfonic acid, C6-C22 sulfonic acid, or xylene sulfonic acid.

14. The method of claim 13, wherein the anionic surfactant is present in the solution in an amount of from about 5 wt % to about 25 wt %, based on the total weight of the solution.

15. The method of claim 1, wherein the solution further comprises an organic acid selected from methane sulfonic acid, ethane sulfonic acid, propane sulfonic acid, butane sulfonic acid, xylene sulfonic acid, benzene sulfonic acid, toluenesulfonic acid, naphthalene disulfonic acid, alkyl sulfonic acids, alkyl diphenyloxide disulfonic acid, cumene sulfonic acid, xylene sulfonic acid, formic acid, acetic acid, glycolic acid, mono-halocarboxylic acids, di-halocarboxylic acids, tri-halocarboxylic acids, picolinic acid, dipicolinic acid, and mixtures thereof.

16. The method of claim 1, wherein the solution further comprises a carboxylic acid selected from furoic acid, salicylic acid, benzoic acid, citric acid, sulfosalicylic acid, sulfosuccinic acid, glycolic acid, lactic acid, formic acid, oxalic acid, malic acid, acetic acid, propionic acid, butanoic acid, pentanoic acid, hexanoic acid, heptanoic acid, octanoic acid, nonanoic acid, decanoic acid, undecanoic acid, dodecanoic acid, as well as their branched isomers, maleic acid, ascorbic acid, alpha-or-beta hydroxy-acetic acid, neopentanoic acid, neoheptanoic acid, neodecanoic acid, malonic acid, succinic acid, glutaric acid, adipic acid, pimelic suberic acid, and mixtures thereof.

* * * * *